(12) United States Patent
Dankerl et al.

(10) Patent No.: US 10,548,555 B2
(45) Date of Patent: Feb. 4, 2020

(54) AUTOMATIC IDENTIFICATION OF A POTENTIAL PLEURAL EFFUSION

(71) Applicant: SIEMENS AKTIENGESELLSCHAFT, München (DE)

(72) Inventors: Peter Dankerl, Baiersdorf (DE); Matthias Hammon, Nürnberg (DE); Martin Kramer, Erlangen (DE); Grzegorz Soza, Heroldsberg (DE)

(73) Assignee: Siemens Aktiengesellschaft (DE)

( * ) Notice: Subject to any disclaimer, the term of this patent is extended or adjusted under 35 U.S.C. 154(b) by 803 days.

(21) Appl. No.: 14/666,684

(22) Filed: Mar. 24, 2015

(65) Prior Publication Data

US 2015/0297164 A1    Oct. 22, 2015

(30) Foreign Application Priority Data

Apr. 17, 2014  (DE) .................... 10 2014 207 449

(51) Int. Cl.
*A61B 6/00* (2006.01)
*A61B 6/03* (2006.01)
*A61B 8/08* (2006.01)

(52) U.S. Cl.
CPC .......... *A61B 6/5217* (2013.01); *A61B 8/5223* (2013.01)

(58) Field of Classification Search
CPC ... A61B 6/5217; A61B 8/5223; G06T 7/0014; G06T 2207/10081; G06T 2207/10132; G06T 2207/20224; G06T 2207/30061
See application file for complete search history.

(56) References Cited

U.S. PATENT DOCUMENTS 6,058,322 A    5/2000  Ashizawa
6,577,752 B2 *  6/2003  Armato, III .......... G06T 7/0012
                                                         382/131

(Continued)

FOREIGN PATENT DOCUMENTS

CN      1663530 A    9/2005
CN    101241596 A    8/2008

(Continued)

OTHER PUBLICATIONS

Chinese Office Action—Application No. 201510144129.4; 4 Pgs.

(Continued)

*Primary Examiner* — Amanda Lauritzen Moher
*Assistant Examiner* — Katherine M McDonald
(74) *Attorney, Agent, or Firm* — Schmeiser, Olsen & Watts LLP (57) ABSTRACT

A method for automatically identifying a potential pleural effusion in medical image data of a thorax of a patient from a scan by means of a medical scanner is provided. It includes at least the steps of accepting rib cage detection data of the rib cage of the patient from the image data, which rib cage detection data include rib cage extent data of a rib cage extent of the interior of the rib cage, accepting lung detection data of the lung of the patient from the image data, which lung detection data comprise lung extent data of a lung extent of the external boundary of the lung, accepting mediastinum detection data of all organs of the mediastinum in the thorax (Th) of the patient from the image data, which mediastinum detection data comprise mediastinum extent data of a mediastinum extent of the external boundary of the mediastinum, and subtracting the lung extent and the mediastinum extent from the rib cage extent while forming pleural effusion identification data.

14 Claims, 4 Drawing Sheets

(56) References Cited

U.S. PATENT DOCUMENTS

| | | |
|---|---|---|
| 8,265,728 B2 | 9/2012 | Armato, III |
| 2004/0086162 A1 | 5/2004 | Doi |
| 2006/0264776 A1* | 11/2006 | Stahmann ............ A61B 5/0031 |
| | | 600/547 |
| 2007/0236490 A1* | 10/2007 | Casteele ............... G06F 19/321 |
| | | 345/418 |
| 2008/0193001 A1 | 8/2008 | Dewaele |
| 2009/0214100 A1* | 8/2009 | Urushiya .............. G06T 7/0012 |
| | | 382/132 |

FOREIGN PATENT DOCUMENTS

| | | |
|---|---|---|
| CN | 102663824 A | 9/2012 |
| CN | 102821697 A | 12/2012 |
| CN | 103377475 A | 10/2013 |
| WO | WO 2008149358 A1 | 12/2008 |

OTHER PUBLICATIONS

Seifert S. et al: Hierarchical parsing and semantic navigation of full body CT data, Proc. SPIE 7259, Medical Imaging 2009: Image Processing, Mar. 27, 2009.

Donohue R. et al: Constrained region-based segmentation of pleural effusion in thin-slice CT, Proceedings of the 2009 13th International Machine Vision and Image Processing Conference (IMVIP '09) / IEEE Computer Society, Washington DC, pp. 24-29; 2009.

\* cited by examiner

AUTOMATIC IDENTIFICATION OF A POTENTIAL PLEURAL EFFUSION

CROSS REFERENCE TO RELATED APPLICATIONS

This application claims priority to DE 102014207449.5 having a filing date of Apr. 17, 2014, the entire contents of which are hereby incorporated by reference.

FIELD OF TECHNOLOGY

The following relates to a method for automatically identifying a potential pleural effusion in medical image data of a thorax of a patient from a scan by means of a medical scanner. It moreover relates to an identification system for such an identification.

BACKGROUND

In medical terms, a pleural effusion is an abnormal collection of liquid in the pleural cavity, which is a narrow gap between the pleurae. The liquid therefore is situated in the rib cage between the lung and the ribs.

In healthy humans, the pleural cavities are filled with a small amount—approximately 5 ml—a high-protein liquid, which, as a type of "lubrication layer", provides freedom of movement to the lungs during inhalation and exhalation.

Smaller pleural effusions (up to a volume of approximately 500 ml) often remain unnoticed. In the case of larger pleural effusions, dyspnea occurs as cardinal symptom, at least in the case of physical exertion. This is due to a reduction in the lung capacity due to the volume taken up in the thoracic cavity by the pleural effusion. The lung is compressed and, as a result, only a smaller portion of the lung tissue is able to take part in the oxygen exchange. Suffocation of the patient may be the result in extreme cases. Therefore, larger pleural effusions are generally "drained" for relief of the patient, i.e. a pleural tap or a thoracentesis is performed, with the aid of which the liquid is discharged from the pleural cavity. By contrast, smaller pleural effusions are treated conservatively, i.e. non-invasively.

Pleural effusions may have varied causes, which may all be referred to as medically relevant. By way of example, they often occur on both sides in the case of cardiac failures; in the case of trauma or cancer, a one-sided pleural effusion can usually be observed. A pleural effusion is often a byproduct of a different disease, which may not necessarily, but only sometimes, result in pleural effusion. A treating or diagnosing practitioner may therefore not necessarily search for a pleural effusion in the case of every patient with a specific disease.

Currently, pleural effusions are usually identified only visually in medical image data as a result of the experience of diagnostic practitioners. Then, there is manual segmentation of the pleural effusion in the image data. Here, use is made, in particular, of CT image data and ultrasound image data. The volume or the extent of a pleural effusion can be established by means of an estimation method, in which a distance measurement value (the axial diameter of the rib cage up to the collapsed lung) in the thorax is multiplied by a selection of possible selectable constants. However, none of these constants were found to be sufficiently correct, and so this determination, just like the manual segmentation, is not only time-consuming but also, moreover, inaccurate.

The article Donohue, Rory/Shearer, Andrew/Bruzzi, John: "Constrained region-based segmentation of pleural effusion in thin-slice CT". Proceedings of the 2009 13$^{th}$ International Machine Vision and Image Processing Conference (IMVIP '09). IEEE Computer Society, Washington D.C., pages 24-29 describes a semiautomatic methodology for distinguishing between tumors and pleural effusions. Here—proceeding from a start point entry by a user—a region growing method is performed. Thus, a user input is necessary here.

Against this background, it is an aspect to provide an alternative option, with the aid of which a potential pleural effusion is identified, in particular automatically and as reliably as possible. Furthermore, it is preferably also an aspect to enable an improved determination of the dimensions of an identified potential pleural effusion.

SUMMARY

An aspect relates to a method of the type set forth at the outset therefore, according to embodiments of the invention, comprises at least the following steps:
  accepting rib cage detection data of the rib cage of the patient from the image data, which rib cage detection data comprise rib cage extent data of a rib cage extent of the interior of the rib cage,
  accepting lung detection data of the lung of the patient from the image data, which lung detection data comprise lung extent data of a lung extent of the external boundary of the lung,
  accepting mediastinum detection data of all organs of the mediastinum in the thorax of the patient from the image data, which mediastinum detection data comprise mediastinum extent data of a mediastinum extent of the external boundary of the mediastinum,
  subtracting the lung extent and the mediastinum extent from the rib cage extent while forming pleural effusion identification data.

The method firmly relates to the identification of a potential pleural effusion. This means that such identification always can be only understood and used as an indication for a medical practitioner, on the basis of which said medical practitioner then assesses and diagnoses whether a pleural effusion is in fact present.

The mediastinum, the mediastinal cavity, is a tissue space in the thoracic cavity extending perpendicularly. It lies in the median plane between the two pleural cavities and extends from the diaphragm to the neck and from the spinal column to the sternum. All thoracic organs with the exception of the lungs, i.e., in particular, the thymus, the large vessels close to the heart, the trachea, the esophagus, lymph nodes, the heart and arteries such as the aorta and a multiplicity of nerve cords, are embedded in the loose connective tissue of the mediastinum.

Each individual one of the aforementioned acceptance steps can respectively consist of simple adoption of detection data, wherein the respective detection data are then already derived in advance, in particular by segmenting the respective organ or the respective structure in the image data using a segmentation method suitable for this purpose. Such methods are known, in particular, from the automatic annotation of image data: for example, Seifert et al. (Seifert, Sascha et al.: "Hierarchical parsing and semantic navigation of full body CT data". Proc. SPIE 7259, Medical Imaging 2009: Image Processing, 275902 (Mar. 27, 2009)) describe a landmark-based parsing and segmentation process for the lung, heart and esophagus, i.e. the major organs in the mediastinum. Analogously, a detection of the rib cage internal dimensions may be performed. The other organs of the mediastinum and optionally the diaphragm can also be segmented in an analogous fashion.

Secondly, each individual one of the aforementioned acceptance steps can also comprise the analysis of the image data and the generation of the respective detection data, i.e. precisely this just-described segmentation. As an alternative to the machine-based, i.e. automatic, segmentation just described in an exemplary manner above, it is also possible (depending on the capabilities of the present system or on the abilities of the user) to perform a semiautomatic or manual generation of the detection data or to adopt detection data thus generated.

As a result of the acceptance steps, extent data in relation to the respective extents of the interior of the rib cage (which also includes the chest muscles around the bones of the rib cage) and of the exterior of the lung and of the mediastinum are provided. Then, the subtraction takes place in the subsequent step. Within the scope thereof, the internal region of the rib cage, as defined by the rib cage extent data, is used as initial datum and the lung extent and the mediastinum extent is then subtracted therefrom. In two-dimensional (2D) image data, e.g. sectional images, this subtraction means a subtraction of the areas: in the respective sectional image, the overall area of the lung and of the mediastinum is subtracted from the internal area of the rib cage present in the 2D image. In three-dimensional (3D) image data, there is a subtraction of the volumes. What remains is a residual region of the overall area or of the overall volume in the respective image data, which residual area is defined as a potential pleural effusion.

Therefore, the invention is not based on a segmentation method, e.g. the aforementioned region growing method, but rather makes use of the tool of subtraction: proceeding from the premise that all other organs or structures in the thorax can be automatically discriminated by means of segmentation or identification algorithms, the region which is non-discriminable (or only discriminable with difficulty) in an analog manner, i.e. the residual region, is identified and denoted as a potential pleural effusion. Thus, the pleural effusion identification data represent this residual region in the image data.

With the aid of the method according to embodiments of the invention, it is readily possible to perform automatic identification of a potential pleural effusion and to do this when carrying out method steps of segmentation, known per se, enriched by the subtraction, which can be performed in an uncomplicated and very precise manner both in terms of calculation and, subsequently, in the image display. Thus, in particular, no further complicated algorithms are required.

The subtraction step can also be described as an assignment of image points, i.e. pixels or voxels, in the image data to a potential pleural effusion, during which only those image points which, firstly, lie in the internal region of the rib cage and, secondly, can be assigned neither to the lung nor to the mediastinum in the thorax are assigned to the potential pleural effusion (and hence to the pleural effusion identification data). Within this meaning, the subtraction can be described as a sequence of yes/no-queries of a classifier at the respective image points.

The subtraction has a geometric and an algebraic aspect: from the subtraction of geometric forms, which are defined by the respective extent data, a new geometric form is derived, which, for example, provides a practitioner interpreting the findings with the information in relation to the point that needs to be punctured if a larger pleural effusion is present in order to drain the pleural effusion. From an algebraic point of view, parameter values can be subtracted from one another, namely parameter values or magnitudes which, in particular, relate to the areas or volumes of extent of the rib cage, lung and mediastinum such that result parameter values in the form of area or volume specifications of the potential pleural effusion emerge.

In particular, using the method according to embodiments of the invention it is also possible to perform a detection of potential pleural effusions without there being an independent suspicion of pleural effusion, i.e. even before a patient complains about lack of breath or other symptoms of a pleural effusion. This is because, as soon as a thorax recording is performed, the question as to whether a potential pleural effusion is present can automatically be clarified as well. This clarification can be of course performed without further scans of the thorax, even without modifying the scan protocols, purely on the basis of the image data of the thorax acquired in any case and with minimal additional calculation complexity. In this sense, embodiments of the invention also serve to prevent discomfort or even further complications. Moreover, additional scans of the patient can be dispensed with.

According to embodiments of the invention, an identification system of the type set forth at the outset comprises at least:

a first acceptance unit or acceptor, embodied to receive rib cage detection data of the rib cage of the patient from the image data, which rib cage detection data comprise rib cage extent data of a rib cage extent of the interior of the rib cage, a second acceptance unit or acceptor, embodied to receive lung detection data of the lung of the patient from the image data, which lung detection data comprise lung extent data of a lung extent of the external boundary of the lung, a third acceptance unit or acceptor, embodied to receive mediastinum detection data of all organs of the mediastinum in the thorax of the patient from the image data, which mediastinum detection data comprise mediastinum extent data of a mediastinum extent of the external boundary of the mediastinum, a subtraction unit which, during operation, subtracts the lung extent and the mediastinum extent from the rib cage extent while forming pleural effusion identification data.

The invention moreover comprises a medical scanner, comprising a recording unit for image acquisition and an identification system according to embodiments of the invention.

Preferably, the identification system is embodied in such a way that it performs a method according to embodiments of the invention fully automatically, i.e. independently. However, it may also operate semiautomatically, i.e. be provided with necessary additional information by additional input from external sources, for example from further logic units, which are optionally linked to databases, and/or by manual entries by a user.

Overall, a majority of the components for realizing the identification system in a manner according to embodiments of the invention, in particular the acceptance units or acceptors and the subtraction unit, can be realized wholly or partly in the form of software modules on a processor. A plurality of the units, in particular the first, second and third acceptance units or acceptors, can also be combined in a common functional unit. By way of example, all three acceptance units or acceptors can be combined to form a common functional unit or any two acceptance units or acceptors can be combined to form a functional unit. Further acceptance units can also be integrated into the identification system (as will be described below). What also applies to these is that they can be embodied both on their own and in combination with any other acceptance unit or acceptor.

Interfaces need not necessarily be embodied as hardware components, but can also be realized as software modules, for example if the image data and/or the respective detection data can be adopted from another component, such as e.g. an image reconstruction device or the like, already realized on the same instrument or if said data only needs to be transferred to another component in terms of software. Likewise, interfaces may consist of hardware and software components, such as e.g. a standard hardware interface which is specifically configured for the specific use by software. Moreover, a plurality of interfaces can also be combined in a common interface, for example an input/output interface.

The invention therefore also comprises a computer program product that is directly loadable into a processor of a programmable identification system, comprising program code means for executing all steps of the method according to embodiments of the invention, when the program product is executed on the identification system.

Further particularly advantageous embodiments and developments of embodiments of the invention emerge from the dependent claims and the subsequent description. Here, the identification system can also be developed according to the dependent claims relating to the method.

Preferably, the method according to embodiments of the invention is developed in that, additionally, diaphragm detection data are received, which comprise diaphragm extent data of a diaphragm extent of the diaphragm of the patient, which diaphragm extent delimits the rib cage extent in the rib cage detection data in the direction of the abdominal cavity of the patient.

This means that a further, fourth acceptance step is carried out in addition to the three aforementioned ones. The diaphragm is also easily discriminable in image data, especially in CT image data. Therefore, by using diaphragm detection data, information in relation to the extent that the thoracic cavity extends in the direction of the abdominal cavity of the patient can be provided. Thus, the diaphragm restricts the volume of the thoracic cavity such that, the thoracic cavity can be completely delimited by combining the rib cage extent data and the diaphragm extent data.

In accordance with a preferred embodiment of the invention,
  the rib cage extent in the rib cage detection data and/or
  the lung extent in the lung detection data and/or
  the mediastinum extent in the mediastinum detection data and/or
  the diaphragm extent in the diaphragm detection data is represented by a surface contour model, preferably by a mesh.

In other words, the rib cage extent data and the lung extent data and the mediastinum extent data and the diaphragm extent data comprise a surface contour model. In an exemplary manner, such a surface contour model represents the contour of the surface of the respective organ or of the mediastinum or of the respective structure. By way of example, it can be realized as a point model, preferably as a mesh, i.e. as a grid, in which an (inner or outer) surface of the relevant organ or of the relevant structure is approximated by a number of smaller, usually very simple elements. The grid thus generated, for example a triangular grid, is then a simplified description of the surface, which can then be used for e.g. further calculations, mainly for the subtraction in the present case. Particularly preferably all the aforementioned extent data respectively comprise a mesh such that the subtraction can be performed continuously on the basis of the generated grid areas. By setting the fineness of the grid, the precision of the pleural effusion identification data can be varied, wherein even a relatively wide-mesh grid with a size of an individual grid area corresponding to that of a voxel generally suffices for being able to make a qualitatively sufficient statement in respect of the potential pleural effusion. By way of example, if a CT scan was made with a slice thickness of 5 mm, then the edge length of each line in the mesh is to be selected to be no more than 5 mm.

In principle, the assumption can be made with high probability that the pleural effusion identification data are already sufficiently meaningful on the basis of the subtraction. In order to refine or secure the significance of the pleural effusion identification data, provision can furthermore be made for detection verification in relation to the extent and/or nature of the potential pleural effusion, to be performed in the pleural effusion identification data after the subtraction. Thus—remaining in mathematical parlance—there is a type of "test", with the aid of which there is verification that the pleural effusion identification data in fact represent a potential pleural effusion.

Within the sequence of the detection verification, it is preferable for the pleural effusion identification data to be adapted in accordance with a detection result of the detection verification. This means that result data, which are obtained from the detection verification, are used to modify the pleural effusion identification data. Such a modification may consist of completely revising the statement that a potential pleural effusion is present, but also of adapting the dimensions, i.e. the extent values of the potential pleural effusion, in the pleural effusion identification data. Such an adaptation of the extent values necessarily causes a reduction in the magnitude thereof.

A first option of the detection verification includes of the detection verification comprising a matching with form data of pleural effusions from a pleural effusion form database.

This pleural effusion form database may have a self-learning embodiment, i.e. it automatically integrates new pleural effusion identification data and is therefore automatically extended. Thus, what is examined is whether the potential pleural effusion represented by the pleural effusion identification data is compatible in terms of its form with typical known forms of pleural effusions obtained from the stored pleural effusion form database. If the form of the potential pleural effusion, which emerges from the pleural effusion identification data, is not unifiable, i.e. compatible, with the forms from the pleural effusion form database, subsequent further detection algorithms may be activated and/or information may be output to a user that the relevant region in the image data should be inspected in more detail.

In an alternative or complementary manner—for example within the meaning of the just-mentioned further detection algorithms—provision can be made for the detection verification to comprise a matching of measurement data in the region of the potential pleural effusion with measurement data typical for a scanning method of the scanner in the case of pleural effusion. By way of example, in the case of measurement data from a computed tomography scanner, the assumption can be made that an HU-value of 0, i.e. the HU-value of water, is measured approximately in the region of the potential pleural effusion. If the HU-value in the region of a potential pleural effusion identified by the pleural effusion identification data deviates significantly, the assumption can be made that the pleural effusion identification data are faulty. Expressed differently, the material density in the region of the identified potential pleural effusion can be used for detection verification; by way of example, this is also a conventional means of detection when identifying the urinary bladder organ.

Then, it is also possible for subsequent further detection algorithms to be activated and/or for information to be output to a user that the relevant region in the image data should be inspected in more detail.

The information stored in the pleural effusion identification data may relate to different levels of insight. A first level of insight relates to a yes/no statement such that the pleural effusion identification data comprise yes/no-information in respect of the presence or absence of the potential pleural effusion. This information per se already suffices for a user in the many cases in which pleural effusions are not firmly sought after. It serves as a warning to and/or as additional information for the user who may draw conclusions about the severity of diseases, which were to be considered originally, purely on the basis of the presence of the potential pleural effusion. Moreover, the user knows that possibly (invasive or conservative) measures may also be necessary for relieving the potential pleural effusion.

Moreover, it is possible to make statements in relation to the location of a potential pleural effusion, namely in particular as to whether a potential pleural effusion is situated exclusively in the right-hand or left-hand thoracic cavity half, or whether it is situated in both halves. This information may be particularly valuable to a treating practitioner because it may allow conclusions to be drawn about the pathological cause of the potential pleural effusion.

Furthermore, namely at a higher level of insight, it is possible to derive a specification in respect of the volume and/or extent of the potential pleural effusion from the pleural effusion identification data. This statement can also be stored in the pleural effusion identification data. The user therefore obtains information enabling an estimation of the quality of the potential pleural effusion. From this, suitable measures for treating the potential pleural effusion can be derived independently therefrom.

Additionally—the underlying information once again lies at a higher level of insight—it is possible to output a signal to a user in the case of a volume of the potential pleural effusion exceeding a volume threshold defined in advance. A particularly preferred threshold is the 500 ml volume of the potential pleural effusion, corresponding with the classification of smaller and larger pleural effusions mentioned at the outset. By way of example, the signal to the user serves as an automatic warning that a larger potential pleural effusion is present and there is a need to act for an (expected) invasive treatment of the potential pleural effusion.

As a last level of insight, various types of additional information in relation to the potential pleural effusion can be derived, in a database-based manner, on the basis of the pleural effusion identification data matched to available reference data from a database. In general terms, the pleural effusion identification data are matched to reference pleural effusion identification data from a database in this case. From this, matching information is then derived. By way of example, the latter may comprise a qualitative and/or quantitative evaluation of the potential pleural effusion present from the pleural effusion identification data, for example an indicator value which may serve the user as a basis of decision-making for making a diagnosis.

In principle, the method according to embodiments of the invention can be performed on the basis of practically all types of medical image data of the thorax, for example on the basis of x-ray images, MRI images, ultrasound images and many more. The medical image data are particularly preferably obtained from a scan by means of a computed tomography (CT) scanner. By way of example, this is advantageous in that the aforementioned organs and structures, namely the rib cage, the lung, the mediastinum and the diaphragm, have in the meantime become well discriminable on the basis of CT image data. Also, a detection verification on the basis of the measurement data can be performed particularly easily in the case of CT images since the CT image reproduces the water present in a pleural effusion with an HU-value of 0, which is an easily detectable reference value. Moreover, it is easier to measure CT image data than e.g. ultrasound data.

BRIEF DESCRIPTION

Some of the embodiments will be described in detail, with reference to the following figures, wherein like designations denote like members, wherein.

DETAILED DESCRIPTION

Figure 1:
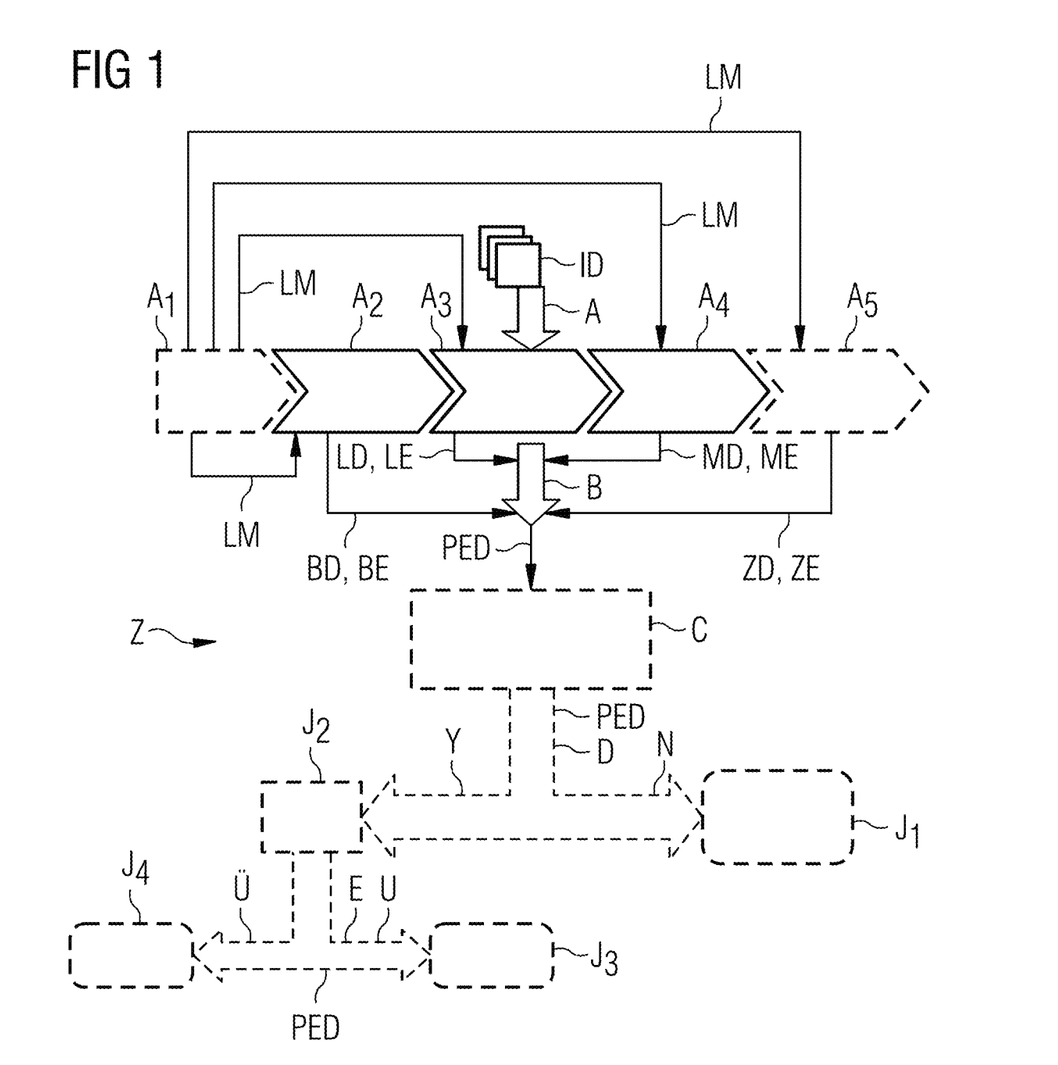
FIG. 1 shows a schematic flowchart of an exemplary embodiment of the method.

FIG. 1 shows a schematic flowchart of an exemplary embodiment of the method Z according to embodiments of the invention for identifying a potential pleural effusion. Here, image data ID of a patient are subjected to an automatic identification of a potential pleural effusion in a step A. This step A comprises a plurality of sub-steps $A_1, A_2, A_3, A_4, A_5$ (some of which are mandatory, some of which are optional). In a first, optional sub-step $A_1$, there is a landmark detection $A_1$ in the image data ID, with the aid of which landmarks LM are extracted, which landmarks may serve for orientation in the image data ID and, in particular, for segmenting individual organs or structures. A second sub-step $A_2$ is an acceptance $A_2$ of rib cage detection data BD of the rib cage of the patient from the image data. These rib cage detection data BD comprise rib cage extent data BE, i.e. data which represent the rib cage extent of the interior of the rib cage of the patient.

This acceptance may comprise segmentation of the rib cage, for example on the basis of landmarks LM detected in the sub-step $A_1$; however, it may also comprise a pure data acceptance of the rib cage detection data BD from a different unit, for example from a segmentation unit or from a data storage means. A similar statement applies analogously to the third to fifth acceptance sub-steps $A_3, A_4, A_5$.

In sub-step $A_3$, there is an acceptance $A_3$ of lung detection data LD of the lung of the patient from the image data ID. The lung detection data LD comprise lung extent data LE, which represent the lung extent of the external boundary of the lung.

The sub-step $A_4$ consists of an acceptance $A_4$ of mediastinum detection data MD of all organs of the mediastinum of the patient in the thorax from the image data ID. The mediastinum detection data MD comprise mediastinum extent data ME, which represent the mediastinum extent of the external boundary of the mediastinum.

An acceptance $A_5$ of diaphragm detection data ZD of the diaphragm of the patient can be seen as optional sub-step $A_5$. The diaphragm detection data ZD comprise diaphragm extent data ZE, which represent the diaphragm extent of the diaphragm.

On the basis of the detection data BD, LD, MD, ZD thus obtained or on the basis of the corresponding extent data BE, LE, ME, ZE, there is a subtraction B in step B, in which the lung extent and the mediastinum extent are subtracted from the rib cage extent. Pleural effusion identification data PED, which represent a potential pleural effusion in the thorax, emerge therefrom.

Optionally, the result of the method Z in the form of the pleural effusion identification data PED can be subjected to detection verification C. Here, the pleural effusion identification data PED can be checked both in terms of the principle statement thereof (is a potential pleural effusion present—yes or no?) and in terms of the statement thereof in respect of an extent and/or nature of the potential pleural effusion. In particular, the detection verification C may comprise checking of the measurement values in the image data ID in the region of the identified potential pleural effusion, i.e. specific measurement values for water are generated as a function of the employed scanner providing the image data ID. If the measurement values in the region of the identified potential pleural effusion do not correspond to the measurement values typical for the respective scanner, there are grounds for suspecting a detection error of a potential pleural effusion. Alternatively or additionally, the detection verification C may comprise matching of the form of the potential pleural effusion, which is represented by the pleural effusion identification data PED, to form data of pleural effusions from a pleural effusion form database. This procedure will still be described in more detail on the basis of FIG. 5.

After passing through the detection verification C, in which the pleural effusion identification data PED may also be adapted in accordance with the detection result of the detection verification C, there is a yes/no-query D in a likewise optional step D. Here, the question as to whether or not a potential pleural effusion is present in the patient is answered on the basis of the pleural effusion identification data PED (which were optionally adapted in the meantime). If this question is answered with no N, no-information $J_1$ may optionally be output, indicating that no potential pleural effusion is present. If the question is answered with yes Y, a yes-information $J_2$ may optionally be output, indicating that a potential pleural effusion is present.

If a potential pleural effusion is present, a quantified query E can be carried out in a further, likewise optional step E on the basis of the pleural effusion identification data PED (which were optionally adapted in the meantime). In said step, an evaluation is carried out as to whether or not the volume of the identified potential pleural effusion lies above a predefined threshold. If the result of this query E is a negative statement U, the presence of a smaller potential pleural effusion can optionally be e.g. indicated by user information $J_3$. Furthermore or alternatively, information may also be output from this that no invasive intervention appears necessary according to the automated assessment. If the result of this query E is a positive statement Ü, user information $J_4$, e.g. a warning signal $J_4$, may optionally be output. Alternatively or additionally, the user information $J_4$ may indicate that a larger potential pleural effusion is present. Furthermore or alternatively, information may also be output from this that an invasive intervention appears necessary according to the automated assessment.

Figure 2:
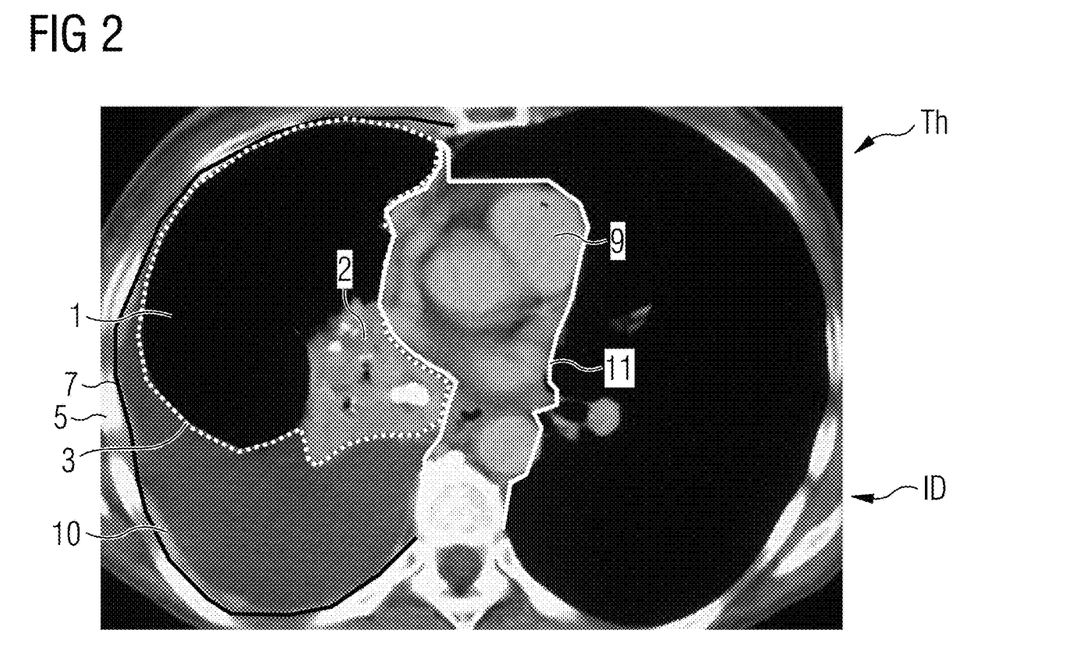
FIG. 2 shows a transverse slice image of a human thorax, with contours of relevant body organs and structures.

FIG. 2 shows a transverse slice image of a human thorax Th from image data ID of a CT scanner. The following organs and structures can be identified therein: the organs and structures of the mediastinum 9 can be identified centrally; said organs and structures are delimited from the other regions of the thorax Th by a delimitation line 11. This delimitation line 11 corresponds to the mediastinum extent data ME. The two pulmonary lobes of the lung 1 are identifiable to the left and right of the mediastinum 9; these are delimited by a delimitation line 3, which corresponds to the lung extent data LE. In the left lung, a collapsed lung region 2 is identifiable approximately centrally in FIG. 2; however said region lies within the delimitation line 3. The rib cage 5 extends around the thorax Th and is delimited on the inner side thereof—in the direction of the thoracic cavity—by a delimitation line 7, which corresponds to the rib cage extent data BE. A pleural effusion 10 is situated in the left-hand region of the thoracic cavity, below the region of the lung but in the thoracic cavity. The delimitation lines 3, 7, 11 are respectively obtained by segmentation methods. They are respectively embodied as a mesh. As a result of this, it is easier to subtract the respective area (or volume) of the lung 1 and of the mediastinum 9 from the area (or from the volume in three dimensions) of the internal space of the rib cage 5. From this subtraction, the pleural effusion which is represented by the pleural effusion identification data PED emerges in a modeled manner.

Figure 3:
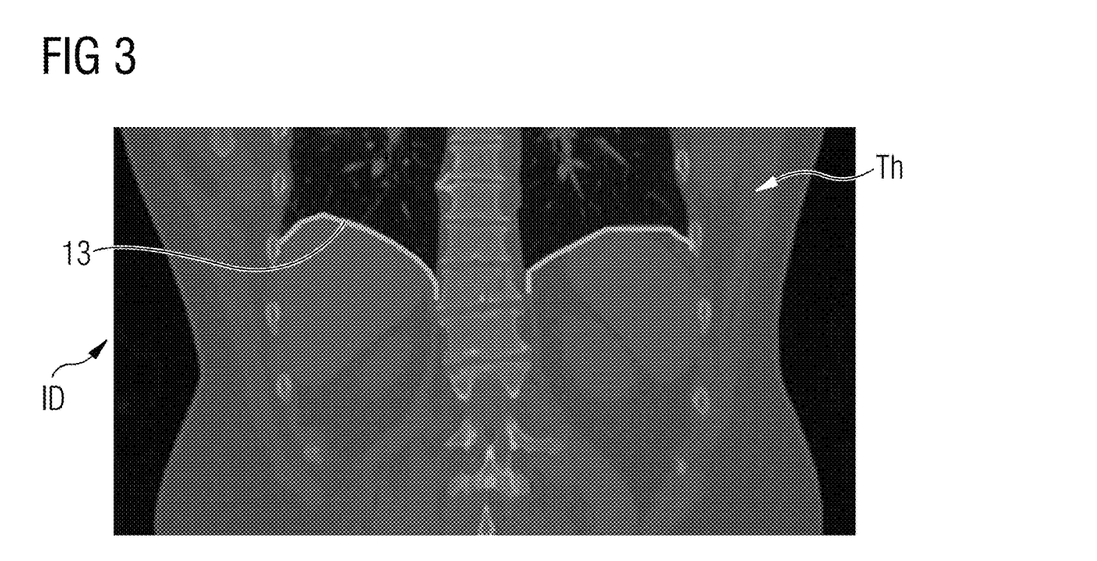
FIG. 3 shows a frontal slice image of a human thorax, with the diaphragm being indicated.

FIG. 3 shows a frontal slice image of a human thorax. A line likewise obtained with the aid of a segmentation method is plotted herein, namely a mesh which represents the extent of the diaphragm 13. The corresponding diaphragm extent data can, as mentioned previously, be used in sub-step $A_5$ for delimiting the region of the thoracic cavity at the base thereof from the abdominal cavity and therefore for obtaining a closed examination volume for this subtraction B.

Figure 4:
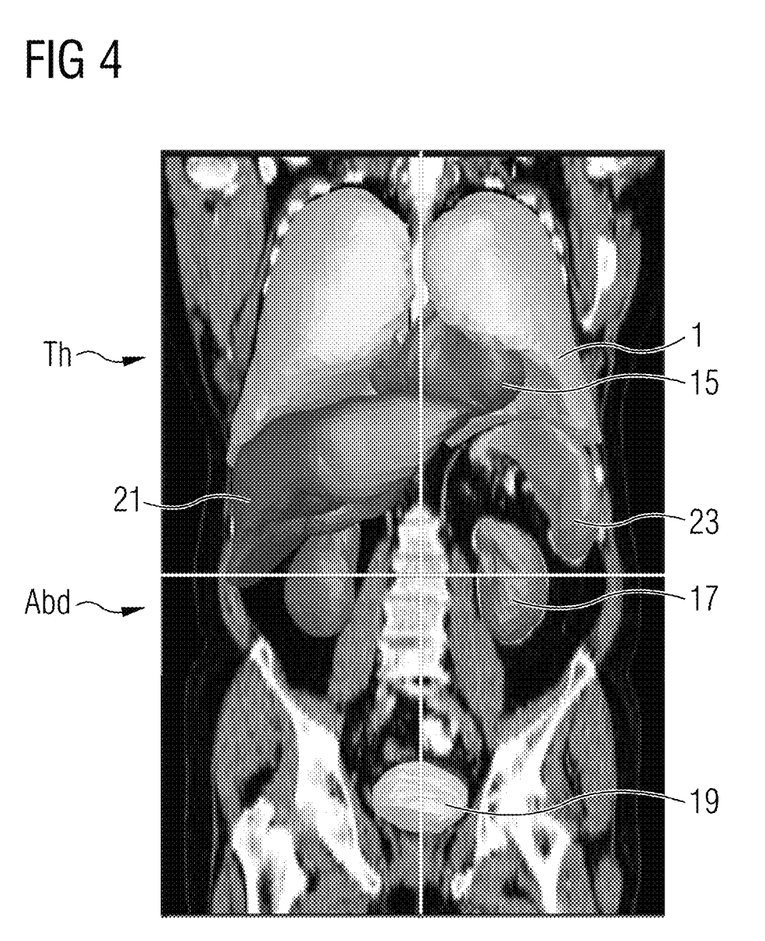
FIG. 4 shows a three-dimensional internal view of a human upper body with specific discriminated organs.

FIG. 4 shows a three-dimensional internal view of a human upper body, comprising the thorax Th and the abdomen Abd with certain discriminated organs 1, 15, 17, 19, 21, 23, the contours of which are once again depicted as meshes or represented thereby. It is possible to identify the lung 1 and the heart 15, which are both situated in the region of the thoracic cavity in the thorax Th. Situated therebelow (in the abdominal cavity, i.e. in the abdomen Abd) are, to the left-hand side in the Figure, the liver 21 and, to the right-hand side in the Figure, the spleen 23. Below these, the kidneys 17 are situated on both sides and the urinary bladder 19 is situated in the pelvic region. All these organs can respectively be segmented individually (or together) with the aid of e.g. landmark-based segmentation algorithms, just like the mediastinum 9 (cf. FIG. 2), which itself is not revealed on its own in the Figure. With the aid of such a segmentation, it is therefore possible to establish detection data or extent data for all the aforementioned structures and organs, of which the detection or extent data in relation to the rib cage 5, in relation to the lung 1 and in relation to the mediastinum 9 and, optionally, in relation to the diaphragm 13 are used within the scope of the exemplary embodiment of the present invention.

Figure 5:
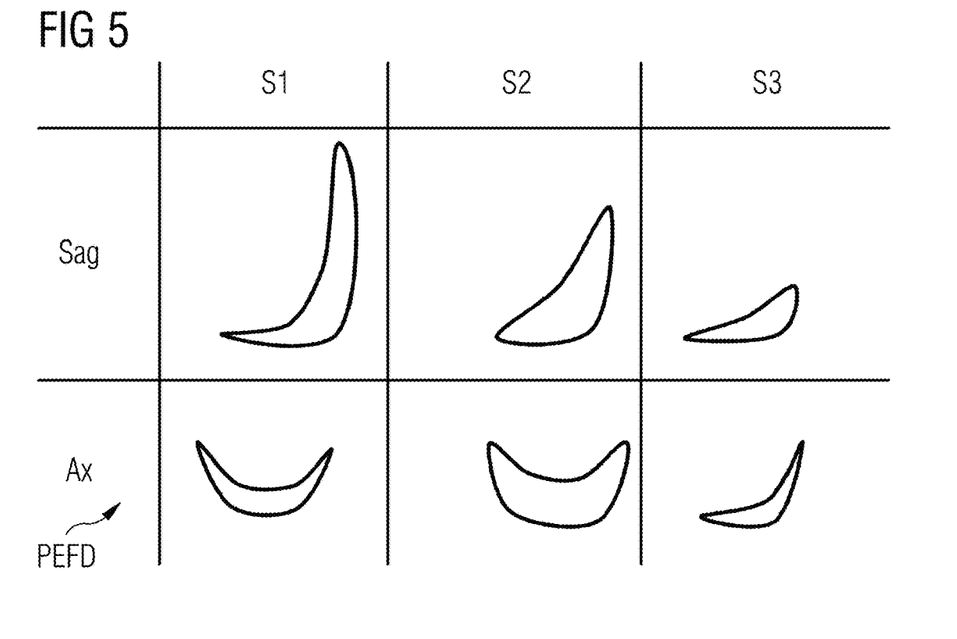
FIG. 5 shows a simple exemplary embodiment of the content of a pleural effusion form database, as can be used in accordance with one exemplary embodiment of the method.

FIG. 5 shows a simple exemplary embodiment of the content of a pleural effusion form database PEFD, as can be used in accordance with one exemplary embodiment of the method according to embodiments of the invention. The pleural effusion form database respectively includes forms of identified pleural effusions for sagittal sections Sag and for axial section Ax of reference patients S1, S2, S3. A potential pleural effusion 10 established within the scope of the method Z according to embodiments of the invention, which is represented by the corresponding pleural effusion identification data PED, can be matched in terms of form to the forms shown here. If the form thereof substantially corresponds to at least one of the three forms depicted here, i.e. due to essential corresponding form features, the assumption can be made in the aforementioned detection verification C that a realistic form of a potential pleural effusion 10 was detected. If it does not correspond thereto, further steps may be performed within the scope of the detection verification C, in particular for adapting the presented pleural effusion identification data PED.

Figure 6:
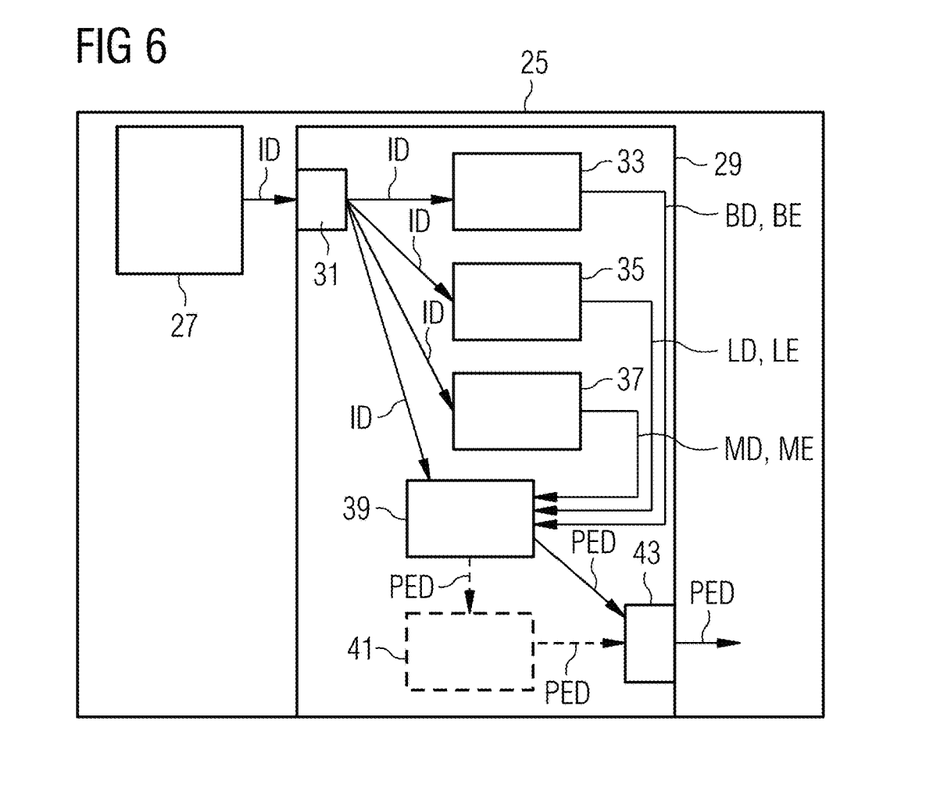
FIG. 6 shows a schematic block diagram of an exemplary embodiment of a scanner, comprising an exemplary embodiment of an identification system.

FIG. 6 shows a schematic block diagram of an exemplary embodiment of a medical scanner 25 according to embodiments of the invention, namely of a computed tomography scanner 25 comprising a (CT) recording unit 27 for image acquisition and an exemplary embodiment of an identification system 29 according to embodiments of the invention.

The identification system 29 includes the following elements: a first acceptance unit 33, a second acceptance unit 35, a third acceptance unit 37 and a subtraction unit 39. Furthermore, it includes an input interface 31 and an output interface 43 and, optionally, a detection verification unit 41.

The functionality of the identification system 29 is explained with reference to the method steps from FIG. 1: image data ID of the thorax Th of a patient are fed from the recording unit 27 into the identification system 29 by way of the input interface 31, and from there said data is forwarded to the three acceptance units 33, 35, 37 and to the subtraction unit 39. The three acceptance units 33, 35, 37 can optionally also be combined to form one or more larger units. Moreover, provision can also be made for a fourth (and optionally also further) acceptance unit(s) (not shown here), which for example can be combined with all or a selection of the previously mentioned three acceptance units 33, 35, 37 depicted in FIG. 6. The first acceptance unit 33 serves for accepting $A_2$ rib cage detection data BD of the rib cage 5 of the patient from the image data ID. The second acceptance unit 35 serves for accepting $A_3$ lung detection data LD of the lung 1 of the patient from the image data ID. The third acceptance unit 37 serves for accepting $A_4$ mediastinum detection data MD of all organs in the mediastinum 9 in the thorax Th of the patient from the image data ID. In particular, a fourth acceptance unit may serve for performing the sub-step $A_5$, i.e. for accepting the diaphragm detection data ZD. The subtraction B takes place in the subtraction unit 39 on the basis of the detection data BD, LD, MD and optionally ZD. The optional detection verification unit 41 performs the detection verification C, on the basis of which it adapts the pleural effusion identification data PED in accordance with the detection result when necessary (i.e. in the case of error detection in the pleural effusion identification data PED). The (optionally adapted) pleural effusion identification data PED are output by the output interface, for example to a user by means of an output unit, such as a printer and/or a monitor display, and/or to an archive system.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method for automatically identifying a potential pleural effusion in medical image data of a thorax of a patient, including at least the following steps:
   providing a medical scanner,
   scanning a patient with the medical scanner so as to receive image data,
   accepting rib cage detection data from the image data, wherein the rib cage detection data includes rib cage extent data of a rib cage extent of an interior of the rib cage of the patient,
   accepting lung detection data from the image data, wherein the lung detection data includes lung extent data of a lung extent of the external boundary of the lung of the patient,
   accepting mediastinum detection data from the image data, wherein the mediastinum detection data includes mediastinum extent data of a mediastinum extent of the external boundary of the mediastinum of all organs of the mediastinum in the thorax of the patient,
   subtracting the lung extent and the mediastinum extent from the rib cage extent to form pleural effusion identification data, wherein the pleural effusion identification data comprises volume information;
   comparing the volume information of the pleural effusion identification data with a volume threshold; and
   outputting a signal when the volume information of the pleural effusion identification data indicates the potential pleural effusion exceeds the volume threshold, wherein the signal serves as an automatic warning that the potential pleural effusion is large and there is a need to act for an invasive treatment of the large potential pleural effusion.

2. The method as claimed in claim 1, wherein additionally, diaphragm detection data are received from the image data, wherein the diaphragm detection data includes diaphragm extent data of a diaphragm extent of the diaphragm of the patient, which diaphragm extent delimits the rib cage extent in the rib cage detection data in the direction of the abdominal cavity of the patient.

3. The method as claimed in claim 2, wherein at least one of:
   the rib cage extent in the rib cage detection data,
   the lung extent in the lung detection data,
   the mediastinum extent in the mediastinum detection data, and
   the diaphragm extent in the diaphragm detection data is represented by a surface contour model.

4. The method as claimed in claim 1, wherein a detection verification, in relation to a potential pleural effusion, is performed in the pleural effusion identification data after the subtracting.

5. The method as claimed in claim 4, wherein the pleural effusion identification data are adapted in accordance with a detection result of the detection verification.

6. The method as claimed in claim 4 wherein the detection verification comprises a matching with form data of pleural effusions from a pleural effusion form database.

7. The method as claimed in claim 4, wherein the detection verification comprises a matching of measurement data in the region of the potential pleural effusion with measurement data typical for a scanning method of the scanner in the case of a pleural effusion.

8. The method as claimed claim 1, wherein the pleural effusion identification data comprise yes/no-information in respect of the presence or absence of the potential pleural effusion.

9. The method as claimed in claim 1, wherein a specification in respect of a volume or extent of a potential pleural effusion is derived from the pleural effusion identification data.

10. The method as claimed in claim 9, wherein a signal is output to a user in the case of a volume of the potential pleural effusion exceeding a volume threshold defined in advance.

11. The method as claimed in claim 1, wherein the pleural effusion identification data are matched to reference pleural effusion identification data from a database and match information is derived therefrom.

12. The method as claimed in claim 1, wherein the image data is obtained from a scan by a computed tomography system.

13. An identification system for automatically identifying a potential pleural effusion in medical image data of a thorax of a patient, including at least a processor, wherein the processor further comprises:
   a first acceptor, configured to receive, from the image data from the medical scanner, rib cage detection data including rib cage extent data of a rib cage extent of the interior of the rib cage of the patient,
   a second acceptor, configured to receive, from the image data from the medical scanner, lung detection data including lung extent data of a lung extent of the external boundary of the lung cage of the patient,
   a third acceptor, configured to receive, from the image data from the medical scanner, mediastinum detection data including mediastinum extent data of a mediastinum extent of an external boundary of the mediastinum of all organs of the mediastinum in the thorax of the patient,
   a subtraction unit configured to, during operation, subtract the lung extent and the mediastinum extent from the rib cage extent to form pleural effusion identification data, wherein the pleural effusion identification data comprises volume information;
   an evaluation unit configured to, during operation, compare the volume information of the pleural effusion identification data with a volume threshold; and
   an output for outputting a signal when the volume information of the pleural effusion identification data indicates the potential pleural effusion exceeds the volume threshold, wherein the signal serves as an automatic warning that the potential pleural effusion is large and there is a need to act for an invasive treatment of the large potential pleural effusion.

14. A computer program product that is on a processor of a programmable identification system comprising a computer readable hardware storage device having computer readable program code stored therein, said program code executable by a processor of a computer system to implement the method as claimed in claim 1, when the program product is executed on the identification system.

* * * * *